United States Patent [19]

Nordfang et al.

[11] Patent Number: 4,831,119

[45] Date of Patent: May 16, 1989

[54] PREPARATION FOR THE TREATMENT OF HEMOPHILIA A INHIBITOR PATIENTS AND A PROCESS FOR PRODUCING SUCH A PREPARATION

[76] Inventors: Ole Nordfang, Selskovvej 6, DK-3400 Hillerod; Mirella E. Rasmussen, Abildgaardsgade 24, DK-2100 Copenhagen 0, both of Denmark

[21] Appl. No.: 881,687

[22] PCT Filed: Nov. 5, 1985

[86] PCT No.: PCT/DK85/00105

§ 371 Date: Jun. 20, 1986

§ 102(e) Date: Jun. 20, 1986

[87] PCT Pub. No.: WO86/02838

PCT Pub. Date: May 22, 1986

[30] Foreign Application Priority Data

Nov. 5, 1984 [DK] Denmark .................... 5253/84

[51] Int. Cl.$^4$ ............... A61K 37/02; A61K 37/04; A61K 35/16; C07K 15/06
[52] U.S. Cl. ............... 530/383; 530/380; 530/381; 424/101; 514/2; 514/21; 514/834
[58] Field of Search ............... 530/383, 381, 380; 424/101; 514/2, 21, 834

[56] References Cited

U.S. PATENT DOCUMENTS 4,649,132 3/1987 Zimmerman .................... 514/12

FOREIGN PATENT DOCUMENTS

84/03628 9/1984 PCT Int'l Appl. .................... 530/383

OTHER PUBLICATIONS

Hoyer, "The Factor VIII Complex: Structure and Function", *Blood*, vol. 58, No. 1, pp. 1-13, 1981.
Kuo et al., "Studies on the Molecular Structure of Human Factor VIII:C", *Thrombosis and Haemostasis*, vol. 50, 1983.
Muller et al, "A Monoclonal Antibody to VIII:C Produced by a Mouse Hybridoma", *Blood*, vol. 58, No. 5, pp. 1000-1006, 1981.
Allain et al., "Response to Factor VIII Infusion in Inhibitor Patients", Progress in Clinical and Biological Research (150), 99-108, 1984.

*Primary Examiner*—Maurice J. Welsh
*Assistant Examiner*—Nathan M. Nutter
*Attorney, Agent, or Firm*—Ladas & Parry

[57] ABSTRACT

A preparation for the treatment of hemophilia A inhibitor patients contains a protein or peptide having a specific Factor VIII:CAg activity of at least 0.5, preferably at least 1 VIII:CAg unit per mg protein, the ratio between the VIII:CAg activity and the VIII:C procoagulant activity being greater than 5:1, preferably greater than 10:1. A fragment of Factor VI-II:C, which displays a doublet of a molecular weight of 80/77 kD in electrophoresis, is reactive hemophilia A inhibitor antibodies and has VIII:CAg activity. This fragment and more low-molecular fragments of Factor VIII:C are capable of neutralizing the coagulation inhibiting effect of all tested antibodies. Such fragments can therefore be used as active component in preparations for providing immunotolerance towards Factor VIII:C in high-dose treatment of inhibitor patients. The peptides are moreover useful as an immunosorbent in specific extracorporeal adsorption treatment of inhibitor patients. The inhibitor reactive peptides can e.g. be recovered from plasma fractions by affinity chromatography, hydrophobic interaction chromatography or cation exchange or they may be biosynthetically and recovered in a similar manner.

23 Claims, 4 Drawing Sheets

VIII:CAg INHIBITION BY INHIBITOR IgG PREPARATIONS.
○ ZHI; △ E; ☐ K.H.; ▽ T.L.; ● A.J.; ▲ B.E.;
■ K.B.; ▼ NORMAL IgG.

FIG. 3

PREPARATION FOR THE TREATMENT OF HEMOPHILIA A INHIBITOR PATIENTS AND A PROCESS FOR PRODUCING SUCH A PREPARATION

The present invention relates to a preparation for the treatment of hemophilia A inhibitor patients and processes for producing such a preparation.

Hemophilia A is a congenital disease which is due to lack of coagulation Factor VIII:C. This factor is present in blood plasma and can be partially purified from blood. Preparations containing this factor (AHF) can be administered to hemophilia A patients so that the patients' blood will be able to coagulate. Production of this type of preparation is described e.g. in the U.S. Pat. No. 3,652,530 and International Application WO No. 84/03628. In these preparations the Factor VIII:C protein typically amounts to 0.1% of the total protein amount. Factor VIII:C of greater purity can be obtained by affinity chromatography (Zimmerman et al., U.S. Pat. No. 4,361,509, Fass et al. Blood 59, 394, 1982).

The Factor VIII:C protein has still not been fully characterized, but part of the structure is known (L. W. Hoyer, Blood 58, 1, 1981; M. Weinstein et al., Proc. Natl. Acad. Sci., USA 78, 5137, 1981; G. Kuo et al., Thromb. Haemostas. 50, 262, 1983). The molecular weight is about 300 kD.

It is known that 10 to 20% of hemophilia A patients do not only lack Factor VIII:C, but also develop antibodies against Factor VIII:C. Such patients are called inhibitor patients, and the antibodies in these patients are called inhibitor antibodies because they inhibit the procoagulant activity of Factor VIII:C (H. R. Roberts & R. Cromartie, Progress in Clinical and Biological Research 150, 1, 1984). The presence of these antibodies causes administration of AHF preparation to have no effect since Factor VIII:C is neutralized, and AHF administration induces increased antibody level.

Inhibitor antibodies can be used as reagents in immunoassays to measure Factor VIII:C antigen (VIII:CAg) (B. Dinesen, C. Fedderson, Thromb. Res. 31, 707, 1983, O. Nordfang et al., Thromb. Haemostas. 50, 111, 1983). An VIII:CAg unit is defined as the content in 1 ml of normal human plasma.

Inhibitor patients have till now been treated:

(a) By non-specific treatment with activated prothrombin complex preparations (FEIBA®, Autoplex®). These preparations contain an unknown component (perhaps Factor VIIa, see U. Hedner and W. Kisiel, J. Clin. Invest. 71, 1837, 1983), which can make plasma coagulate in spite of large inhibitor amounts. However, activated prothrombin complex preparations cannot help all inhibitor patients, and the patients are not cured of their inhibitor. Moreover, the use of this type of preparations involves a great risk of thrombosis.

(b) It has been found that the inhibitor formation can be suppressed by administration of very large doses of AHF (100 to 200 units/kg daily). This makes it possible to induce immunotolerance of Factor VIII (H. H. Brackman & J. Gormsen, Lancet, p. 933, 1977). After this type of treatment the patient can be treated with AHF preparations like other hemophiliacs. However, high dosis AHF treatment is also non-specific because very large doses of irrelevant protein are administered, and the patients cannot utilize the procoagulant activity in AHF preparations during the treatment.

At the beginning of the treatment phase the inhibitor level increases, and is then gradually reduced to zero. Bleedings cannot be prevented with AHF during the treatment, but bleedings can be partly stopped with the above-mentioned FEIBA® (factor eight inhibitor bypassing activity) preparations.

This treatment is very expensive (typically U.S. $600,000 per patient, see S. Stenbjerg et al., Thromb. Res. 34, 533, 1984) and has accordingly found little application.

The invention is based on the surprising finding that a component from plasma fractions having Factor VIII:CAg reactivity and only little or no Factor VIII:C procoagulant activity is reactive to 7 of 7 antibodies from inhibitor patients. Therefore, the suppression treatment will be just as effective if a preparation is administered which contains a suitably high amount of VIII:CAg without significant VIII:C procoagulant activity.

Accordingly, the preparation of the invention contains a protein or peptide having a specific Factor VIII:CAg activity of at least 0.5 VIII:CAg U/mg, preferably at least 1 VIII:CAg U/mg, and is characterized in that the ratio between the Factor VIII:CAg activity and the Factor VIII:C activity is greater than 5:1, preferably greater than 10:1. The preparation is preferably essentially free of Factor VIII:C procoagulant activity.

In the formulation of the preparation to an injectable solution, the VIII:CAg concentration is usually adjusted to more than 10 U/ml, preferably more than 50 U/ml.

Admittedly, it is known that prothrombin complex preparations, such as FEIBA®, which can be administered concurrently with the Factor VIII treatment of inhibitor patients, also contains VIII:CAg, cf. Allain et al., Progress in Clinical and Biological Research 150, 99, 1984, but the content is generally of the order of only 4.5 VIII:CAg U/ml. However, the FEIBA preparations also contain significant amounts of Factor VIII:C procoagulant activity (Barrowcliffe et al., Thromb. Res. 21, 181–186, 1981), which is believed to play an important role for the effect. Barrowcliffe has measured an VIII:CAg concentration of 2 U/ml and a Factor VIII:C activity of 1.3 U/ml, corresponding to a ratio of 1.5:1.

Prothrombin complex preparations also contain a number of other coagulation factors, in particular Factor II, VII, IX and X as well as possibly Factor VIIa, IXa, and Xa (Aronson, Progress in Clinical and Biological Research 150, 243, 1984) which conceivably promote coagulation of hemophilia A plasma and are therefore also used for stopping bleedings in hemophilia A patients.

As stated, the preparation of the invention exhibits a VIII:CAg to VIII:C ratio of at least 5:1, preferably at least 10:1, and is, as mentioned, preferably essentially free of VIII:C activity. Usually, the preparation is free of other coagulation factors and do not promote coagulation of hemophilia A plasma, cf. Table 1 below. If desired, coagulation factors, such as those mentioned above, can be added to obtain the known additional effects of the factors.

The protein with VIII:CAg reactivity, which is used as an active ingredient in the preparation, may e.g. be a Factor VIII:C fragment which in SDS-PAGE exhibits a doublet of an approximate molecular weight of 80/77 kD, or a fragment thereof which can be obtained by thrombine activation and exhibits a doublet of an approximate molecular weight of 70/67 kD, cf. Kuo et al. loc. cit.

It appears from Kuo et al. that the 80/70 kD fragment exhibits VIII:CAg activity against a specific inhibitor antibody (zHI) and no procoagulant activity. However, it could not be expected from this that the fragment, as demonstrated below, is capable of blocking the inhibition activity of 7 of 7 inhibitor antibodies.

According to the invention, recovery of the 80/77 kD fragment with VIII:CAg reactivity from plasma fractions can take place in several ways, e.g. by affinity chromatography, hydrophobic interaction chromatography or by cation exchange. The starting material can in principle be any VIII:CAg-containing fraction, but is expediently a cryosupernatant or a plasma fraction obtained by precipitation of redissolved cryoprecipitate with 2 to 6% by weight, preferably about 4% by weight of PEG. The latter is particularly expedient because this precipitate is normally not used during the further plasma fractionation.

The invention is not limited to the use of the 80/77 kD fragments of Factor VIII:C. As further explained below it is shown on FIG. 1*b* that also smaller Factor VIII:C fragments are reactive against inhibitor antibodies. Likewise it may be expected that other inhibitor antibodies are reactive against other parts of the Factor VIII:C molecule. Thus Factor VIII:C isolated from blood plasma contains a 92 kD fragment (Zimmerman et al. U.S. Pat. No. 4,361,509). To the extent such fragments are capable of blocking inhibitor antibodies such as shown in Table 5 below they are part of the invention.

Neither is the invention limited to the use of Factor VIII:C fragments isolated from blood plasma. Based on the DNA sequence of Factor VIII:C partial fragments of the Factor VIII:C gene may be produced. These partial-fragments may be inserted in suitable vectors (e.g. plasmids or vira). These vectors may be inserted in suitable host cells (e.g. E. Coli or yeast or CHO, COS or other mammalian cells), rendering the cells capable of producing partial fragments of Factor VIII:C. It may be expected that such fragments are capable of blocking inhibitor antibodies such as shown in Table 5 without containing essential amounts of Factor VIII:C procoagulant activity, since they have the same molecular structure as the corresponding peptide sequences isolated from blood plasma. Consequently, such fragments may also be used in preparations according to the invention.

Reactivity of antibodies

Several authors (H. P. Muller et al., Blood 58, 1000, 1982; B. Sola et al., Proc. Natl. Acad. Sci., USA 79, 1983, 1982) have described production of monoclonal antibodies against Factor VIII:C. These antibodies can be obtained after immunization of mice with Factor VIII by fusing spleen cells with tumor cells, as described by Köhler & Milstein (Nature 256, 495, 1985). Use of this technique has resulted in the production of monoclonal antibodies against Factor VIII:C, called 42 IgG, 47 IgG and 56 IgG, respectively.

BRIEF DESCRIPTION OF THE DRAWINGS

FIG. 1*a* Autoradiogram of SDS gel of factor VIII:C subjected to VIII:C antibodies FIG. 1*b* Autoradiogram of SDS gel of decomposed VIII:C subjected to VIII:C antibodies FIG. 2 Graph of VIII:CAg inhibition by inhibitor IgG preparations FIG. 3 SDS—PAGE (Polyacrylamide) gel of eluted fractions of IgG Sepharose Chromatography of VIII:-CAg FIG. 1*a* shows a solid phase immunoisolation with monoclonal antibodies. Plastic beads were coated with antibody against mouse immunoglobulin/monoclonal antibody. After washing the beads were incubated with $^{125}$I labelled.

Factor VIII:C. Factor VIII:C was produced as described by E. Tuddenham et al., J. Lab. Clin. Med. 93, 40, 1979. After washing the beads were extracted with a SDS sample buffer, and the eluates were run on a SDS gel. The figure shows an autoradiogram of SDS gel:

Lane 1: Tracer. ($^{125}$I labelled Factor VIII:C). Lane 2: Normal mouse IgG; Lane 3: 42 IgG; Lane 4: 47 IgG; Lane 5: 56 IgG.

It appears from FIG. 1*a* that these antibodies bind the 80/77 kD component of Factor VIII:C (lanes 3, 4, 5). This is the same component as is bound by a human inhibitor antibody, zHI.

FIG. 1*b* shows a solid phase immunoisolation performed like the test in FIG. 1*a* with zHI bound to the bead and with a decomposed VIII:C sample. It appears from FIG. 1*b* that other peptides than 80/77 kD doublet with VIII:CAg activity against zHI (70/67 kD and other decomposition products) may occur in a decomposed sample.

FIG. 2 shows that 7 of 7 inhibitor antibodies are capable of blocking the binding of zHI in an VIII:CAg inhibition assay. Since the zHI antibody binds the 80/77 kD doublet, the other inhibitor antibodies must also have reactivity against this fragment of Factor VIII:C. The assay was carried out as follows: Wells in microtiter plates were coated with zHI immunoglobulin. After washing Factor VIII:C containing plasma was added, and after another washing inhibitor immunoglobulin was added together with peroxidase labelled zHI antibody. Complete binding of peroxidase labelled zHI is obtained by addition of buffer instead of inhibitor immunoglobulin.

Affinity chromatography of VIII:CAg

It has been found in adsorption of AHF with monoclonal 47 IgG coupled to Sepharose that only the VIII:-CAg is absorbed and not the coagulation active Factor VIII:C (Table 1). This is surprising because the antigen is present both on Factor VIII:C and VIII:CAg. However, the antigen appears to be more accessible on the coagulation inactive VIII:CAg than on VIII:C.

TABLE 1

Specific VIII:CAg adsorption to 47 IgG coupled to Sepharose

| | AHF | | Unbound | | EG/NaCl eluate | |
|---|---|---|---|---|---|---|
| Immunosorbent | VIII:C | VIII:CAg | VIII:C | VIII:CAg | VIII:C | VIII:CAg |
| 47 IgG/Cl 2B | 88 | 270 | 90 | 90 | 0.32 | 138 |
| Control Cl 2B | 88 | 270 | 77 | 248 | 0.14 | 0.09 |

Table 2 shows that a number of salts can be used together with ethylene glycol (EG) to elute VIII:CAg from immunosorbent with monoclonal antibody. MgCl$_2$, which is sparingly soluble in EG, can be used for elution without EG present.

TABLE 2

Effect of different salts on ethyleneglycol elution from 56 IgG

| Sample | VIII:CAg units |
|---|---|
| AHF (Nordiocto ®) | 210 |
| Flow through | 140 |
| Eluate, 50% EG/saturated NaCl | 22 |
| —, 50% EG/saturated KCl | 19 |
| —, 50% EG/2 M KI | 3.6 |
| —, 50% EG/2 M CaCl$_2$ | 2.2 |
| —, 2M MgCl$_2$ | 22 |
| —, 50% EG/saturated NaAc | 24 |

With 56 IgG coupled to sepharose it is possible to purify VIII:CAg from cryosupernatant. Cryosupernatant contains 0.4 VIII:CAg U/ml, and less than 1 ppm of the total protein is VIII:CAg. Table 3 shows that 8000-fold purification can be obtained in one step, enabling production of a preparation with a specific VIII:CAg activity of 61 units VIII:CAg/mg protein. This is a significantly higher specific activity than is found in existing AHF preparations.

In the production of high purity (HP) preparations from less purified AHF, i.a. a 4% PEG precipitate may occur (U.S. Pat. No. 3,652,530, International Application No. WO 84/03628). This precipitate contains VIII:CAg, and, as appears from Table 3, it is possible to use this precipitate as a starting material for VIII:CAg purification. With just 0.25 ml of immunosorbent it is possible to purify 920 VIII:CAg units from 140 ml of redissolved 4% PEG precipitate. The resulting preparation has a secific VIII:CAg activity of 6,900 units VIII:CAg/mg protein.

With human inhibitor IgG coupled to Sepharose Cl 2B it is also possible to purify VIII:CAg from redissolved 4% PEG precipitate (Table 3). The yield of VIII:CAg, however, is smaller than in the use of monoclonal antibody, since 50% ethylene glycol with 2.5M NaCl is not able to quantitatively elute the bound VIII:CAg. The above tests are described more fully in the following examples 2-4.

TABLE 3

Purification of VIII:CAg from various starting materials by means of 56 IgG and human inhibitor IgG

| Fraction | VIII:CAg | Protein mg, E$_{280}$ | spec. act. units/mg |
|---|---|---|---|
| (Ex. 2) | | | |
| Cryosup., 500 ml | 200 | 30,000 | 0.007 |
| Cryosup. flow through, 500 ml | 100 | 30,000 | 0.003 |
| EG/NaCl eluate from 56 IgG, 2 ml | 39 | 0.64 | 61 |
| (Ex. 3) | | | |
| 4% PEG prec., 140 ml | 1500 | 5,200 | 0.29 |
| 4% PEG prec., flow through, 140 ml | 340 | 5,200 | 0.07 |
| EG/NaCl eluate from 56 IgG, 1 ml | 920 | 0.131 | 6900 |
| (Ex. 4) | | | |
| 4% PEG prec., 110 ml | 1000 | 3,400 | 0.29 |
| 4% PEG prec. flow through, 110 ml | 340 | 3,400 | 0.10 |
| EG/NaCl eluate from human inhibitor, 1 ml | 68 | 0.082 | 830 |

The invention also concerns a process for producing a Factor VIII:CAg preparation for the treatment of hemophilia A inhibitor patients, which is characterized by treating a Factor VIII:CAg-containing solution, e.g. a plasma fraction with an immunosorbent comprising antibodies which are specific to Factor VIII:CAg, bound to solid particles and then desorbing the bound VIII:CAg by elution with a buffer and processing it to a preparation. Processing usually requires change to a physiological buffer. This can e.g. be done by drying, dialysis, gel filtration or ion exchange.

Human inhibitor antibodies or monoclonal antibodies preferably 56 IgG or 47 IgG, can be used as the immunosorbent.

Hydrophobic interaction chromatography of VIII:CAg and cation exchange

VIII:CAg can be purified from VIII:CAg containing solutions e.g. plasma fractions without using affinity chromatography with antibodies. Thus, it has been found that 77/80 kD Factor VIII:CAg is extremely basic and hydrophobic. These properties can be utilized for recovery of Factor VIII:CAg from plasma fractions by hydrophobic interaction chromatography and cation exchange, cf. also the following example 5.

Hydrophobic chromatography

May be performed according to the invention at a pH from 6 to 9.5, but the binding is strongest at a high pH, e.g. pH 8.5. A hydrophobic gel is used such as phenyl sepharose (Pharmacia). The binding to phenyl sepharose can take place without addition of a salt, but is improved significantly by addition of NaCl. 0.3M NaCl addition to the cryosupernatant is suitable since it will not interfere with the later recovery of other plasma proteins, such as albumin and immunoglobulin G. When using a 4% PEG precipitate from redissolved cryoprecipitate, higher NaCl concentrations may be employed. The bound Factor VIII:CAg is eluted with a buffer, e.g. under the conditions stated in example 5 below.

Cation exchange

May be performed according to the invention below 8.0 since this gives the best binding. A suitable value is pH 5.5 since pH in the cryosupernatant can be reduced to this value without impairing VIII:CAg.

A strong cation exchanger may be used, such as "Whatman ®SE53". The bound Factor VIII:CAg is eluted with a buffer, e.g. under the conditions stated in example 5 below.

Both of these methods result in very selective purification of Factor VIII:CAg, and give a very pure eluate. A particularly expedient method of additional concentration of the VIII:CAg activity consists in combining a hydrophobic chromatography and cation exchange, as described in the foregoing and illustrated in examples 5 and 6 below. In this case a weaker cation exchanger is preferred, e.g. "CM fast flow sepharose".

As appears from example 5 and Table 4 these two purification methods utilize various properties in VIII:CAg and give in combination an 1100-fold purification from the cryosupernatant. Like affinity chromatography, these purification methods can be applied to all VIII:CAg-containing solutions, e.g. plasma fractions, cf. Table 4, which both shows purification of cryosupernatant and the precipitate from 4% PEG precipitation of redissolved cryoprecipitate.

TABLE 4

Purification of VIII:CAg by hydrophobic interaction chromatography and cation exchange

| Fraction | VIII:CAg units | Protein mg, $E_{280}$ | spec. act. units/mg |
|---|---|---|---|
| (Ex. 5) | | | |
| Cryosup | 1100 | 160,000 | 0.007 |
| Flow-through from phenyl-Sepharose | 390 | 160,000 | 0.002 |
| Eluate from phenyl-Sepharose | 440 | 2,100 | 0.21 |
| Flow-through from SE 53 | 50 | 2,000 | 0.04 |
| Eluate from SE 53 | 300 | 37.5 | 8.0 |
| 4% PEG prec. | 798 | 3,000 | 0.26 |
| Flow-through from phenyl-Sepharose | 36 | 2,400 | 0.02 |
| Eluate from phenyl-Sepharose | 560 | 83 | 6.7 |
| Flow-through from SE 53 | 64 | 83 | 0.77 |
| Eluate from SE 53 | 380 | 1.83 | 210 |

Effect of VIII:CAg according to the invention

In vitro coagulation inhibition experiments indicate that the purified VIII:CAg according to the invention will also have effect in vivo. In coagulation inhibition assay, the coagulation inhibiting effect of inhibitor IgG on normal plasma is measured. The dilution giving 50% inhibition is stated in Bethesda units (C. K. Kasper et. al. Thromb. Diath. Haemorr. 34, 860, 1972). Table 5 shows a comparative experiment in which normal plasma was incubated with about 3 Bethesda units of inhibitor IgG from 6 different inhibitor patients and as a control with the zHI IgG previously described. The experiments were conducted with and without presence of a preparation according to the invention containing 100 VIII:CAg U/ml. It appears from the table that the purified VIII:CAg of the invention has a distinct inhibitor suppressing effect on all the antibodies with respect to the experiments without VIII:CAg. Thus, the Bethesda titer of all the antibodies is reduced by more than 25%. This shows that the inhibitor effect of all the 7 tested antibodies is due to reactivity against the 80/77 kD ingredient of Factor VIII:C.

TABLE 5

Suppresion of coagulation inhibition with 80/77-VIII:CAg

| Inhibitor IgG | % VIII:C after incubation without VIII:CAg | % VIII:C after incubation with VIII:CAg |
|---|---|---|
| HZ (zHI) | 0 | 82 |
| AJ | 6 | 89 |
| KB | 17 | 61 |
| E | 0 | 71 |
| THL | 10 | 95 |
| KH | 5 | 80 |
| BE | 6 | 76 |
| Normal IgG | 100 | 102 |

The above-mentioned 7 antibodies were deposited on Oct. 30, 1984 at Statens Seruminstitut (the State Serum Institute) of Copenhagen under No. 50-KR-306.

Use of VIII:CAg as an immunosorbent

It is possible to remove Factor IX inhibitor antibodies from the blood of a Factor IX inhibitor patient by circulating blood through a column to which Factor IX is coupled, C. Freiburghaus, Thromb. Haemostas. 50, 208, 1983.

On the other hand, it is not possible specifically to remove Factor VIII inhibitor antibodies correspondingly. This is due to several reasons:

(1) The molecular weight of Factor VIII in AHF preparations is usually 1,000 to 20,000 kD, since the preparation also contains Factor VIII:RAg. Therefore, Factor VIII couples very poorly to gels.

(2) In coupling a Factor VIII complex, VIII:CAg can be coupled via VIII:RAg or other parts of Factor VIII. Accordingly, VIII:CAg will easily be washed from the coupled gel during use.

These circumstances do not apply to VIII:CAg purified as described here.

Therefore, VIII:CAg according to the invention bound to a suitably solid matrix, such as a sepharose gel, will be suitable as an immunosorbent, e.g. in extracorporeal specific adsorption treatment of Factor VIII inhibitor patients.

The production of preparations according to the invention by the various methods described above is further illustrated in the following examples, from which some of the results obtained have already been summarized in the preceding tables.

Example 1

Figure 1A:
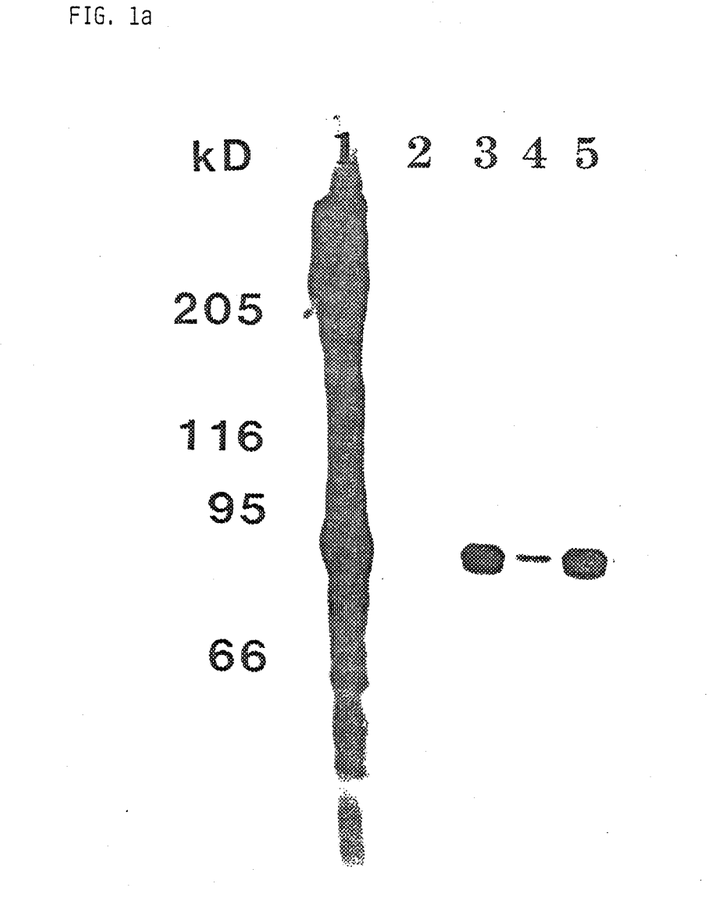
Figure 1B:
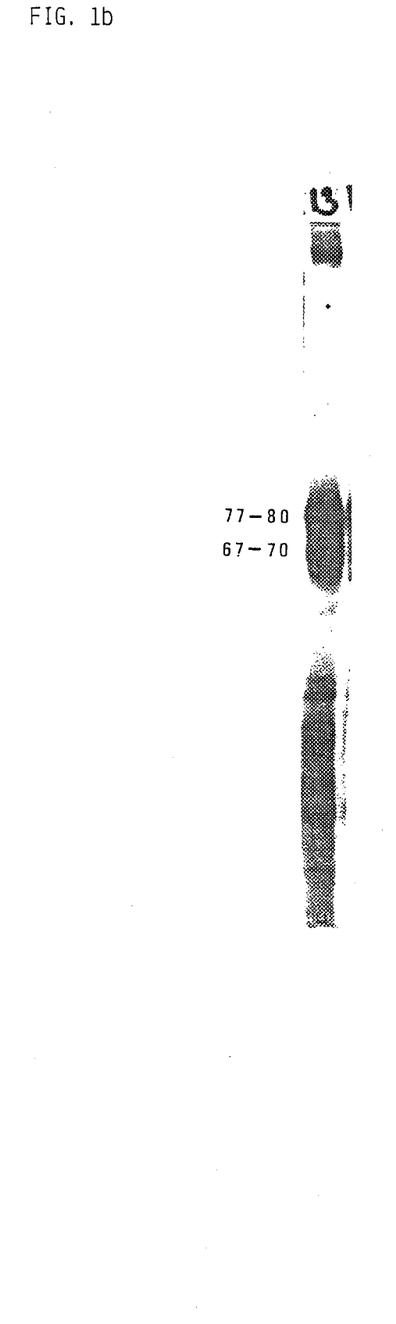
Figure 2:
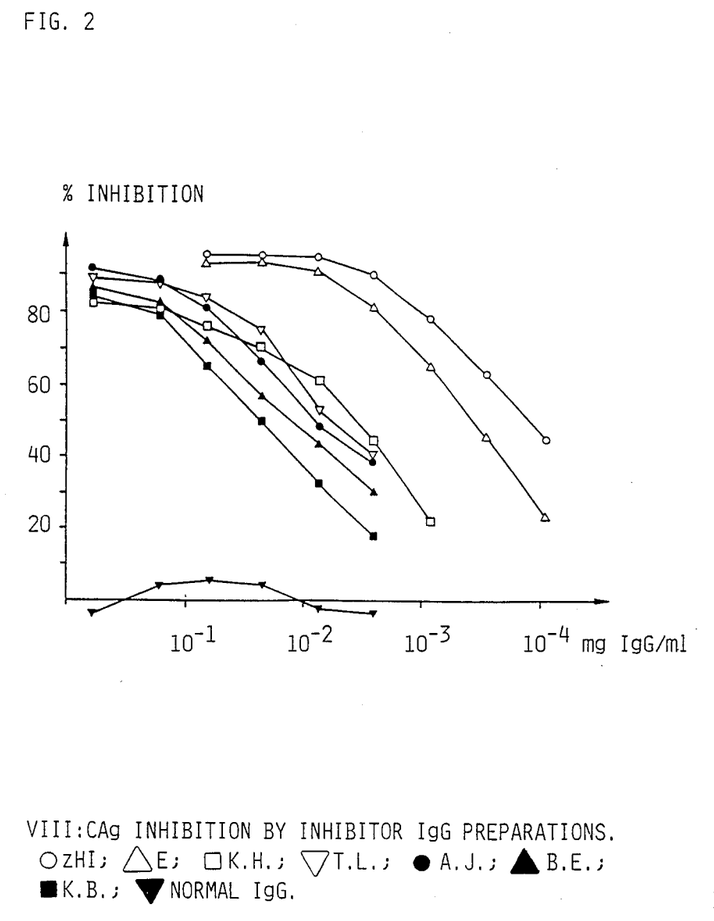
Figure 3:
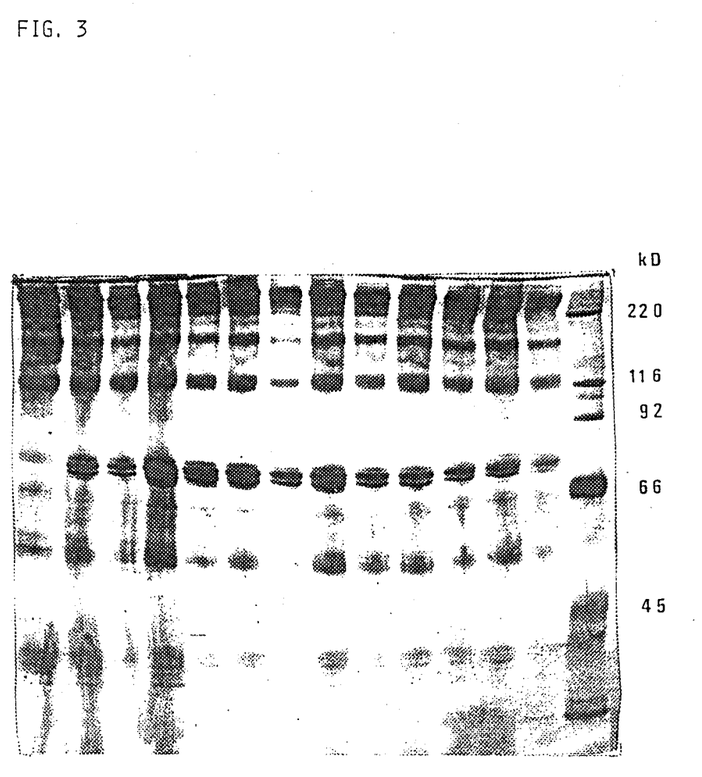

5 mg of 47 IgG are coupled to 5 ml of Sepharose 4B activated with 0.5 g of CNBr. After blocking with 1M glycine, pH 8.5 and washing with elution buffer cyclus, the gel is incubated overnight with 100 ml of AHF (Nordiocto ®) containing 400 VIII:CAg U/ml. The gel is washed on a column with 20 ml of buffer A (20 mM imidazole, 10 mM $CaCl_2$, 0.15M NaCl, 0.02% $NaN_3$, pH=7.35) and 100 ml of a buffer A with 0.5M NaCl. The gel is eluted with buffer A with 0.5M NaCl in 50% EG. 6 ml of eluate contain 7200 units of VIII:CAg. FIG. 3 shows SDS-PAGE of eluted fractions. Evaluated by the colour intensities more 25% of the protein in the eluate is 80/77 kD protein.

Example 2

0.5 mg of 56 IgG are coupled to 0.5 ml of Sepharose 2B/Cl. After blocking and washing with elution buffer cyclus the gel is incubated overnight with 500 ml of cryosupernatant (plasma after cryoprecipitation) containing 200 VIII:CAg units (Spec. act.: 0.007 VIII:CAg U/mg). The immunosorbent is isolated from the cryosupernatant by passing the incubation mixture through a column, produced from a 2 ml disposable syringe. The flow through contains 100 VIII:CAg units. After washing with 2 ml of buffer B (50 mM imidazole, 0.15M NaCl, 0.02% $NaN_3$, pH=7.35) and 100 ml of buffer B with 2.5M NaCl, elution is effected with 2.5 ml of buffer B with 2.5M NACl in 50% EG. The eluate contains 39 VIII:CAg units (Spec. Act. 61 U/mg) and 0.5 unit VIII:C procoagulant activity, cf. also Table 3 above.

Example 3

Redissolved cryoprecipitate is absorbed with $Al_2O_3$ and is precipitated with 4% PEG, as described in the International Application WO No. 84/03628. The precipitate is redissolved by stirring for 45 min. with ¼ cryovolume of buffer B with 0.5M NaCl and 10 mM EDTA. Cloudiness is removed by centrifugation, and the redissolved precipitate containing 1,500 VIII:CAg units (Spec. act.: 0.29 U/mg) is incubated overnight with 0.25 ml "Sepharose 4B" gel coupled with 5 mg of 56 IgG/ml. The gel is collected, as described in example 2, and the flow through contains 340 VIII:CAg units.

The gel is washed with 3 ml of buffer B and 2 ml of buffer B with 2.5M NaCl. Elution is performed with 1.1 ml of buffer B with 2.5M NaCl in 50% ethylene glycol. The eluate contains 920 VIII:CAg units, and the specific activity is 6900 U/mg, cf. also Table 3 above.

Example 4

A 4% PEG precipitate from an AHF process containing 1000 VIII:CAg units is redissovled in buffer B with 0.5M NaCl and 10 mM EDTA. After redissolution, incubation is effected overnight with 0.25 ml of "Sepharose Cl 2B" gel coupled with 10 mg of human inhibitor IgG/ml. The gel is collected, as described in example 2, and the flow through contained 340 VIII:CAg units. The gel is washed and eluated, as described in example 3. The eluate contains 68 VIII:CAg units, and the specific activity is 830 U/mg, cf. also Table 3 above.

Example 5 (see table 4)

2.6 l of cryosupernatant containing 1100 VIII:CAg units are admixed with 5 mM ethylene glycol-bis-(beta-aminoethylether)-N,N'-tetra acetic acid (EGTA)/0,3M NaCl, and pH is adjusted to 8.5. 180 ml of phenyl Sepharose (Pharmacia) are added and incubated for 1 hour. The gel is collected on a column and washed with 400 ml of 5 mM imidazole/0.45M NaCl, pH 7.4 and eluted with 250 ml of 50% ethylene glycol/5 mM imidazole/pH 7.4. The eluate contains 440 units of VIII:CAg with a specific activity of 0.21 U/mg protein.

The pH of the eluate is adjusted to 5.5, and 25 ml of cation exchanger of the "Whatman ®SE53" type are added and incubated for 30 minutes. The ion exchanger is collected on a column and washed with 50 ml of 50 mM phosphate/5 mM EGTA/pH 7.4. VIII:CAg is eluted with 35 ml of 1M NaCl/50 mM phosphate/5 mM EGTA/pH 7.4. The eluate contains 300 units of VIII:CAg with a specific activity of 8.0 U/mg protein.

Example 6

500 g of 4% PEG precipitate from an AHF process according to International Application WO No. 84/03628 (from 300 l of plasma) are redissolved in 3.7 l of 50 mM phosphate/0,75M NaCl/5 mM EDTA/pH 8.5. pH is adjusted to 8.5 with 9.5M NaOH, and, after filtration through filter paper, the solution contains 17,500 VIII:CAg units and 190,000 mg of protein (specific activity 0.09 U/mg protein). The redissolved precipitate is passed through a column with 250 ml of phenyl Sepharose gel with a flow of 3.7 l/h. The phenyl Sepharose is washed with 1.3 l of 25 mM phosphate/5% ethylene glycol/pH 7.4 with a flow of 3.7 l/h. 13.500 VIII:CAg units with 2,000 mg of protein (specific activity 6.8 U/mg protein) are eluted in 1.3 l of 25 mM phosphate/65% ethylene glycol/pH 7.4. The eluate is admixed with NaCl to a concentration of 50 mM, and pH is adjusted to 7.0. The eluate is passed through a cation exchanger column with 6.25 ml "CM fast flow Sepharose" (Pharmacia) with a flow rate of 500 ml/h. The column is washed with 60 ml of 10 mM phosphate/50 mM NaCl/pH 7.3 at a flow of 500 ml/h. 10,800 VIII:CAg units with 4.9 mg of protein (specific activity 2,200 U/mg) are eluted in 18 ml of 5 mM phosphate/0.5M NaCl/7½% saccharose, pH 7.3 (600 VIII:CAg U/ml).

The eluate is admixed with human albumin to a concentration of 0.5%, is sterile filtrated and dispensed into 3 bottles containing 6 ml each. After freeze drying the preparation is heat treated at 68° C. for 72 hours. Each bottle is dissolved in 18 mg of sterile $H_2O$ and contains 190 VIII:CAg U/ml.

Example 7

VIII:CAg is produced as described in example 6, except for the use of 50 mM $NaHCO_3$ 0.5M NaCl, pH 7.3 to elute the Cm ion exchanger. pH of the eluate is adjusted to 8.5, and 4800 VIII:CAg units in 3 ml of eluate are coupled to 1 ml of CNBr activated "Sepharose 4B". The coupled gel is blocked with 1M glycine pH 8.5.

200 $\mu$l of VIII:CAg Sepharose 4B gel was incubated for 2 hours at 37° C. with 6.4 ml of plasma from a Factor VIII inhibitor patient. Before incubation, the plasma contained inhibitor antibodies in an amount of 22 BU/ml. After incubation the inhibitor amount was reduced to 1.8 BU/ml. After reactivation with 3M $NH_4SCN$ the 200 $\mu$l of VIII:CAg Sepharose 4B gel were reincubated for 2 hours at 37° C. with 6.4 ml of plasma from the same Factor VIII inhibitor patient. In this incubation the inhibitor titer was reduced to 3.5 BU/ml.

We claim:

1. Preparation for the treatment of hemophilia A inhibitor patients, comprising a protein or peptide having a specific Factor VII:CAg activity of at least 0.5 U/mg protein, wherein the ratio between the Factor VIII:CAg activity and the Factor VIII:C procoagulant activity is greater than 5:1.

2. Preparation according to claim 1, wherein said preparation is essentially free of factor VIII:C procoagulant activity.

3. Preparation according to claim 1 wherein said preparation is essentially free of other coagulation factors or their activated forms.

4. Preparation according to claim 1 wherein the protein with factor VIII:CAg activity activity is a fraction of the Factor VIII:C molecule having a molecular weight of 80/77 kD or 70/67 kD, determined by SDS—PAGE and containing the antigenic sites of factor VIII:C.

5. Preparation according to claim 1 wherein the protein with Factor VIII:CAg activity is a biosynthetically produced peptide sequence containing the antigenic site(s) prepared using recombinant DNA techniques.

6. Preparation according to claim 1 wherein the Factor VIII:CAg activity is at least 50 U/ml.

7. A process for producing a preparation comprising a protein or peptide having a specific Factor VII:CAg activity of at least 0.5 U/mg protein, comprising treating a Factor VIII:CAg-containing solution with an immunosorbent comprising antibodies which are specific to Factor VII:CAg, bound to a solid carrier and then desorbing the bound VIII:CAg by elution with a buffer, isolating the protein and mixing it with a pharmaceutically acceptable carrier.

8. A process according to claim 7, wherein the immunosorbent comprises human inhibitor antibodies or monoclonal antibodies.

9. A process for producing a preparation comprising a protein or peptide having a specific Factor VII:CAg activity of at least 0.5 U/mg protein, wherein the ratio between the Factor VIII:CAg activity and the Factor VIII:C procoagulant activity is greater than 5:1 comprising subjecting a Factor VIII:CAg-containing solution to cation exchange chromatography, isolating the protein and mixing it with a pharmaceutically acceptable carrier.

10. A process according to claim 9, wherein a Factor VIII:CAg-containing solution which has been purified by chromatography on a hydrophobic gel is used as the factor VIII:CAg preparation.

11. A process according to claim 7 wherein a cryosupernatant plasma fraction is used as the Factor VIII:CAg-containing solution.

12. A process according to claim 7 wherein the Factor VIII:CAg-containing solution is a plasma fraction obtained by precipitation of a redissolved cryoprecipitate with 2 to 6% by weight of PEG.

13. A method for treating hemophilia A inhibitor patients comprising administering an effective amount of a preparation comprising a protein or peptide having a specific Factor VIII:CAg activity of at least 0.5 U/mg protein, wherein the ratio between the Factor VIII:CAg activity and the Factor VIII:C procoagulent activity is greater than 5:1, to such patients.

14. The method, as in claim 13 wherein said preparation is essentially free of factor VIII:C procoagulent activity.

15. The method, as in claim 13 wherein the protein with Factor VIII:Cag activity is a fraction of the factor VIII:C molecule having a molecular weight of 80/77 kd or 70/67 kd, determined by SDS-PAGE, and containing the antigenic sites of Factor VIII:C.

16. The method, as in claim 13, wherein the protein or peptide having specific factor VIII:Cag activity is a fragment of Factor VIII:C.

17. Preparation according to claim 1, wherein the ratio is greater than 10:1.

18. Preparation according to claim 1 wherein said preparation is essentially fee of factor II, VII, IX or X or their activated forms.

19. Preparation according to claim 4 wherein the protein with factor VIII:CAG activity is a biosythetically produced peptide sequence, produced using recombinant DNA technology.

20. A process according to claim 8 wherein the immunosorbent comprises 56 IgG or 47 IgG.

21. A process according to claim 7 wherein a plasma fraction obtained by precipitation of a redissolved cryoprecipitate of about 4% by weight of PEG is the factor VIII:Cag containing solution.

22. The method as in claim 1, wherein the protein or peptide having a specific factor VIII:Cag activity is a fragment of Factor VIII:C.

23. An immunosorbent for removing inhibitor antibodies comprising a Factor VIII inhibitor neutralizing polypeptide substantially without Factor VIII coagulant activity.

* * * * *